(12) United States Patent
Ahn et al.

(10) Patent No.: US 7,695,572 B2
(45) Date of Patent: Apr. 13, 2010

(54) DISHWASHER AND CONTROLLING METHOD THEREOF

(75) Inventors: Byung Hwan Ahn, Kimhae-si (KR); Soung Bong Choi, Changwon-si (KR); Deung Hee Lee, Kimhae-si (KR); Hung Myoung Cho, Kimhae-si (KR); Hyeok Deok Kim, Changwon-si (KR); Seong Hae Jeong, Changwon-si (KR)

(73) Assignee: LG Electronics Inc., Seoul (KR)

( * ) Notice: Subject to any disclaimer, the term of this patent is extended or adjusted under 35 U.S.C. 154(b) by 862 days.

(21) Appl. No.: 11/442,608

(22) Filed: May 30, 2006

(65) Prior Publication Data

US 2007/0102025 A1    May 10, 2007

(30) Foreign Application Priority Data

May 31, 2005   (KR) ................... 10-2005-0046131
May 31, 2005   (KR) ................... 10-2005-0046136

(51) Int. Cl.
*B08B 3/00* (2006.01)
*F26B 19/00* (2006.01)
*F26B 21/02* (2006.01)

(52) U.S. Cl. ............. 134/58 D; 134/102.1; 34/77; 34/231; 34/233

(58) Field of Classification Search ............ 134/18, 134/25.2, 56 D, 94.1, 184, 58 D, 102.1; 34/77, 34/218, 219, 231, 233
See application file for complete search history.

(56) References Cited

U.S. PATENT DOCUMENTS

| | | | | |
|---|---|---|---|---|
| 1,755,101 A | * | 4/1930 | Fording et al. | 34/187 |
| 3,049,136 A | * | 8/1962 | Van Scoyk | 134/95.2 |
| 3,072,128 A | * | 1/1963 | James | 134/57 D |
| 5,337,500 A | * | 8/1994 | Enokizono | 34/77 |
| 2009/0095332 A1 | * | 4/2009 | Lee | 134/105 |

* cited by examiner

*Primary Examiner*—Michael Barr
*Assistant Examiner*—Saeed T Chaudhry
(74) *Attorney, Agent, or Firm*—McKenna Long & Aldridge LLP (57) ABSTRACT

A dishwasher and a controlling method thereof are provided. The dishwasher includes a tub, a door, a steam generator, and a dish storage. The tub holds dishes and is opened at one end. The door selectively seals the opened end of the tub. The steam generator is provided outside the tub to generate steam. The steam discharger discharges the steam generated by the steam generator into the tub. The dish storage stores dishes to be sterilized by the steam discharged from the steam discharger.

11 Claims, 9 Drawing Sheets

DISHWASHER AND CONTROLLING METHOD THEREOF

This application claims the benefit of Korean Patent Application No. 10-2005-0046136, filed on May 31, 2005 and Korean Patent Application No. 10-2005-0046131, filed on May 31, 2005, which are hereby incorporated by reference for all purposes as if fully set forth herein.

BACKGROUND OF THE INVENTION

1. Field of the Invention

The present invention relates to a dishwasher, and more particularly, to a dishwasher with a built-in steam generator. In further detail, the dishwasher and its controlling method supply hot steam to its dishwashing compartment, diversifying the dishwasher's functions and improving its dishwashing effectiveness.

2. Description of the Related Art

A dishwasher is a home appliance that sprays high-pressure wash liquid to wash and remove food residue and other impurities left on surfaces of dishes. A filter filters the food residue, and the wash liquid is recirculated. Detergent is dissolved into the wash liquid to facilitate the removal of food residue.

In order to improve the above dishwashing process, the following dishwasher functions have been developed.

First, by heating wash liquid to aid in dissolving the detergent, overall dishwashing effectiveness can be improved. Also, by heating wash liquid, the wash liquid can more easily remove glutinous rice and other hardened food residue.

Furthermore, by dividing the wash cycle of a dishwasher into a pre-wash cycle and a main wash cycle, the pre-wash cycle soaks hardened food residue, so that it can be more easily removed in the main wash cycle. Another method being employed is removing germs and sterilizing dishes by emitting ultraviolet light onto the surfaces of dishes.

However, despite the above devised methods according to the related art, the problem of increasing dishwashing effectiveness remains. Especially in oriental households, where in many cases, the staple food is glutinous rice, the latter is difficult to effectively remove from dishes, exasperating the problem of dishwashing efficiency of dishwashers according to the related art. Even the use of hot water to soak food residue cannot completely obviate the above problem. Also, because soaking requires a prolonged amount of time, it lengthens the duration of the wash cycle.

The above problems reduce the overall washing efficiency of a dishwasher.

SUMMARY OF THE INVENTION

Accordingly, the present invention is directed to a dishwasher and controlling method thereof that substantially obviate one or more problems due to limitations and disadvantages of the related art.

An object of the present invention is to provide a dishwasher and a controlling method thereof that allow food residue hardened on dishes in the dishwasher to be easily removed, thereby increasing dishwashing effectiveness.

Another object of the present invention is to provide a dishwasher and a controlling method thereof that quickly perform a soaking function, so that the duration of a wash cycle is reduced to be more convenient for a user.

A further object of the present invention is to provide a dishwasher with a region in a tub that receives highly concentrated steam in order to increase sterilization efficiency, and a method of controlling the dishwasher.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided dishwasher including: a tub for holding dishes and opened at one end thereof; a door for selectively sealing the opened end of the tub; a steam generator provided at an outside of the tub, for generating steam; a steam discharger for discharging the steam generated by the steam generator into the tub; and a dish storage for storing dishes to be sterilized by the steam discharged from the steam discharger.

In another aspect of the present invention, there is provided a dishwasher including: a tub forming a wash compartment within and opened at an end thereof; a door for selectively opening and closing the opened end of the tub; a sterilizing space provided inside the tub; and a steam generator for generating steam to supply to the sterilizing space.

In a further aspect of the present invention, there is provided a controlling method of a dishwasher, including: storing dishes in a dish storage inside a tub; and supplying steam to an inside of the dish storage and sterilizing the stored dishes through a predetermined button manipulation.

Because the dishwasher according to the present invention can satisfactorily clean dishes in physical, chemical, and biological terms, it is more efficient to use this dishwasher.

Also, because a ventilating fan is used to circulate the steam in a predetermined direction, a sterilizing effect can be achieved inside the dishwasher.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
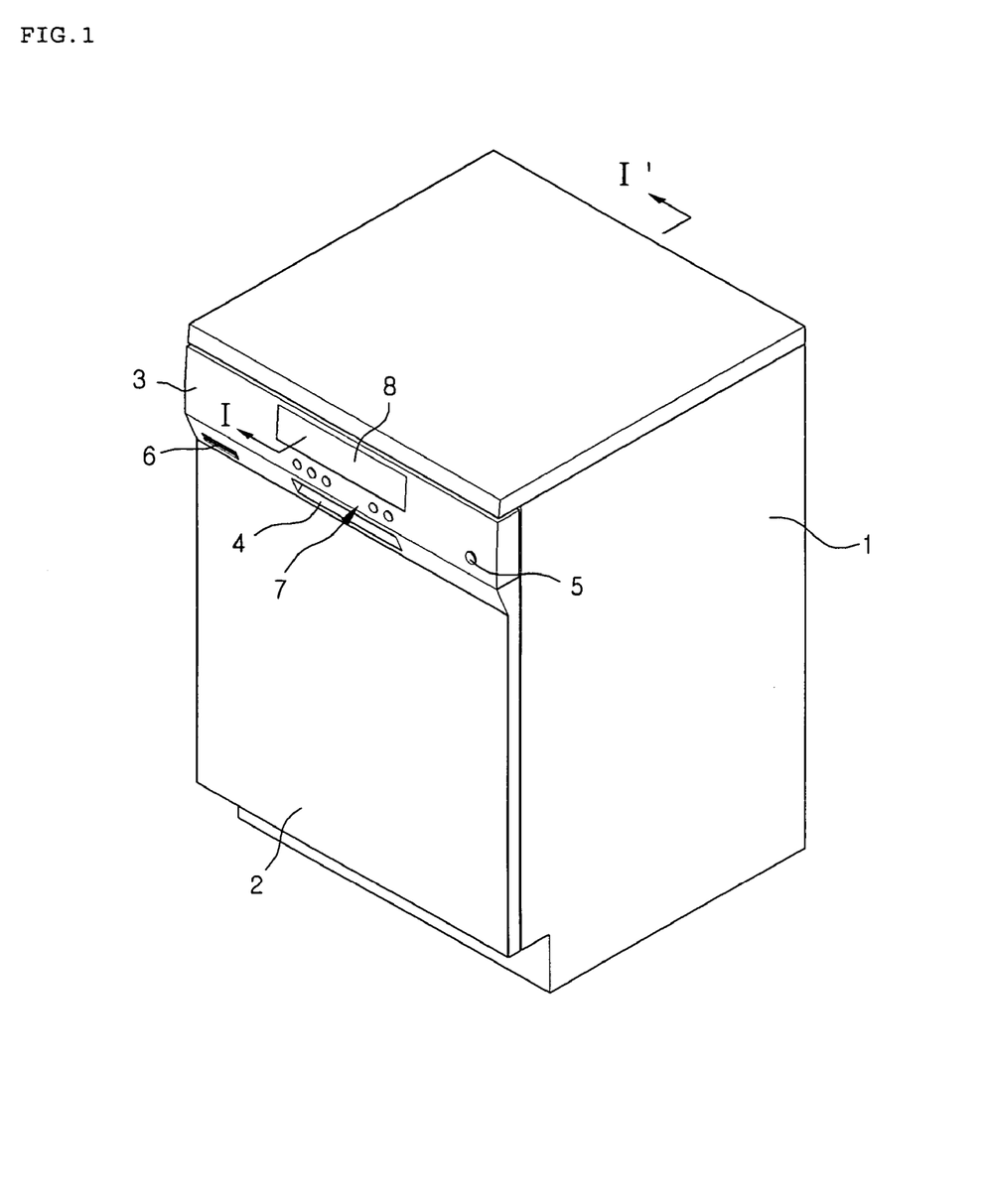
FIG. 1 is a perspective view of a dishwasher according to the present invention.

FIG. 1 is a perspective view of a dishwasher according to the present invention.

Referring to FIG. 1, a dishwasher according to the present invention includes a case 1 forming an outer shape of the dishwasher and an opening at a front thereof, a door 2 sealing the opening at the front of the case 1, and a control panel 3 provided above the door 2, for displaying and controlling the operation of the dishwasher.

In detail, the control panel 3 includes a power switch 5 for switching power to the dishwasher on and off, a door handle 4 used to open and close the door 2, controls 7 for implementing a predetermined operation of the dishwasher according to a user's manipulation thereof, a display 8 for displaying the operation of the dishwasher, and a steam discharge hole 6 for exhausting hot air from inside the dishwasher.

Figure 2:
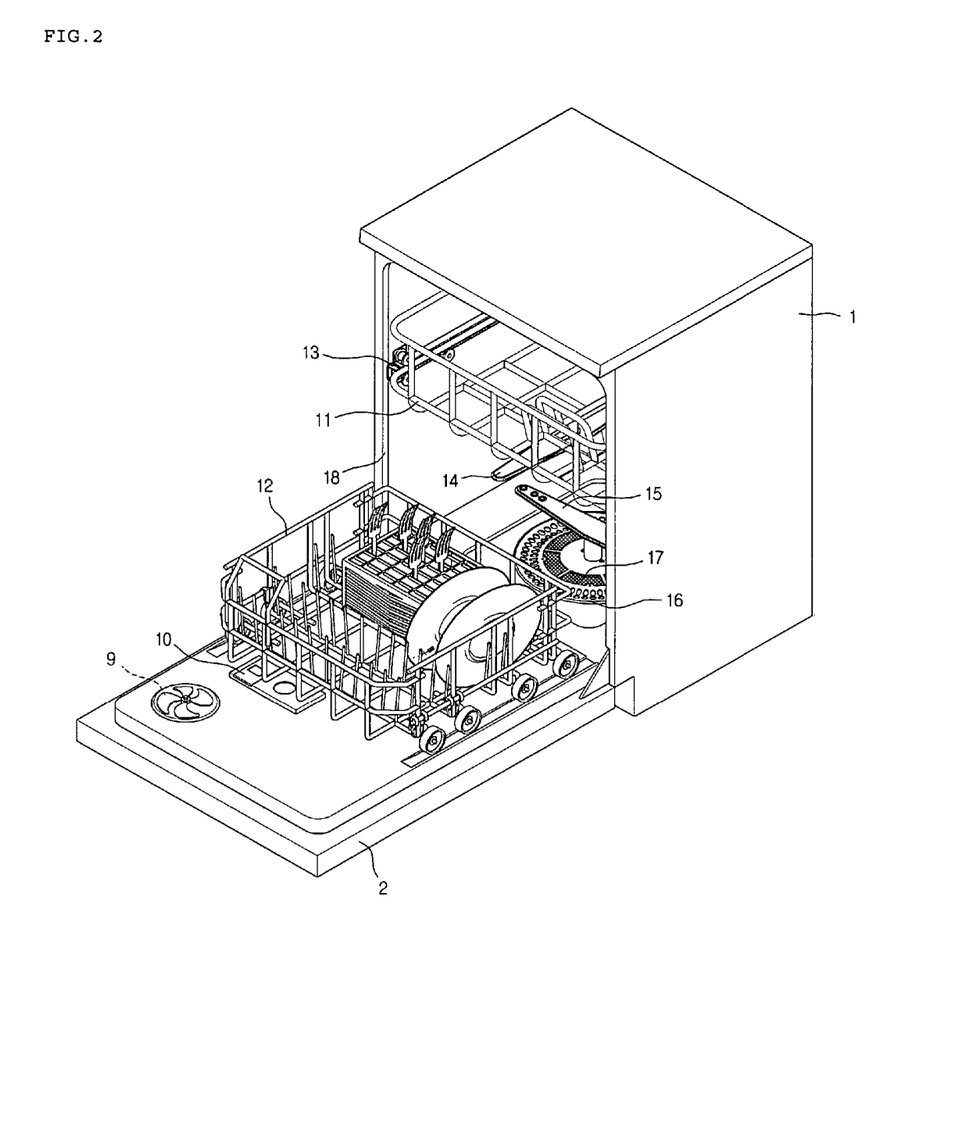
FIG. 2 is a perspective view of a dishwasher according to the present invention with its door open.

FIG. 2 is a perspective view of a dishwasher according to the present invention with its door open.

Referring to FIG. 2, a tub 18 for containing wash liquid inside the dishwasher is disposed therein, and a sump 16 disposed at the bottom of the tub 18 for collecting, filtering, and re-circulating wash liquid to be sprayed.

In detail, the inside of the tub 18 includes an upper dish rack 11 and a lower dish rack 12 for placing dishes in, and an upper spray arm 14 and a lower spray arm 15 for spraying wash liquid respectively towards the upper and lower dish racks 11 and 12.

The inner surfaces of the tub 18 have a rail 13 extending from front to rear in order to slide the upper dish rack 11 thereon. A filter 17 is disposed at the bottom of the tub 18 to filter impurities from wash liquid.

A water guide 19 (in FIG. 3) is provided on an inner side surface of the tub 18 to supply the upper spray arm 14 with wash liquid.

The door 2 is coupled to the case 1 through a hinge (not shown) at the bottom of the door 2, so that a user can pivot the door about the hinge in an upward or downward direction by pushing or pulling. A ventilating fan 9 formed in a predetermined location on the door 2 forcefully circulates or expels air inside the tub 18. Also, a detergent cup 10 for holding detergent is formed in the inner surface of the door 2, and supplies a predetermined amount of detergent into the tub 18 during the operation of the dishwasher.

Figure 3:
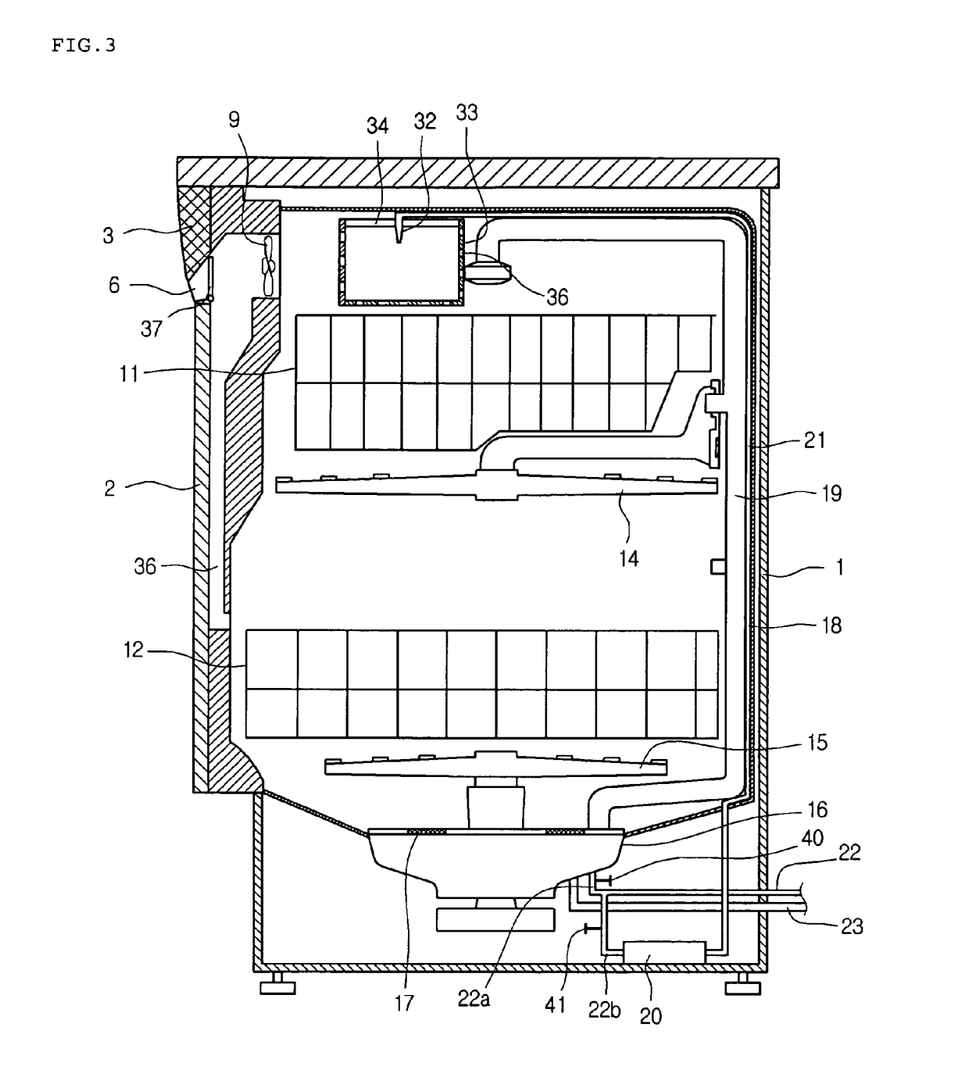
FIG. 3 is a sectional view taken along line I-I' in FIG. 1.

FIG. 3 is a sectional view taken along line I-I' in FIG. 1.

Referring to FIG. 3, a dishwasher according to the present invention further includes a main water supply pipe 22 connecting the tub 18 and a water supply outside of the dishwasher to supply water into the tub 18, a water discharge pipe 23 for discharging wash liquid (that has been used for dishwashing and is contaminated) to the outside of the dishwasher, a steam generator 20 for generating steam and disposed on a surface below the tub 18, and a steam supply pipe 21 for supplying the steam generated by the steam generator 20 to the inside of the tub 18.

In detail, the steam supply pipe 21 forms a steam discharger 32 for discharging steam at one end thereof. The steam discharger 32 is located at the top of the tub 18. Accordingly, even when wash liquid is discharged into the tub 18, the wash liquid does not enter the steam supply pipe 21. The steam supply pipe 21 extends vertically and in parallel with the water guide 19 along the rear inner surface of the tub 18.

The main water supply pipe 22 branches into a tub water supply pipe 22a and a steam water supply pipe 22b. The tub water supply pipe 22a has a tub water regulating valve 40 formed thereon that regulates the amount of water supplied to the tub 18, and the steam water supply pipe 22b has a steam water regulating valve 41 that regulates the amount of water supplied to the steam generator 20.

The tub 18 includes a sterilizing box 33 that forms a space separate from the rest of the tub 18, provided at a top portion of the tub 18. The steam discharger 32 is located inside the sterilizing box 33. Accordingly, dishes contained inside the sterilizing box 33 can be completely sterilized with the steam discharged from the steam discharger 32.

Through-holes 36 are provided in each surface of the sterilizing box 33 to discharge condensing moisture within the sterilizing box 33 to the outside thereof.

A door passage 36 is formed within the door 2, into which air from inside the tub 18 enters and is discharged back into the tub 18. The ventilating fan 9 is provided at the top of the door passage 36.

The ventilating fan 9 provided inside the door passage 36 suctions the air inside the tub 18 and discharges it towards the sterilizing box 33 during a sterilizing course. Conversely, after the sterilizing course has been completed, the air inside the tub 18 is expelled to the outside by the ventilating fan 9.

Here, in order to perform the two functions described above, the door passage 36 communicates with a steam discharge hole 6. A damper 37 for selectively opening and closing the steam discharge hole 6 or the door passage 36 may be provided within the door passage 36 on the steam discharge hole 6.

Figure 4:
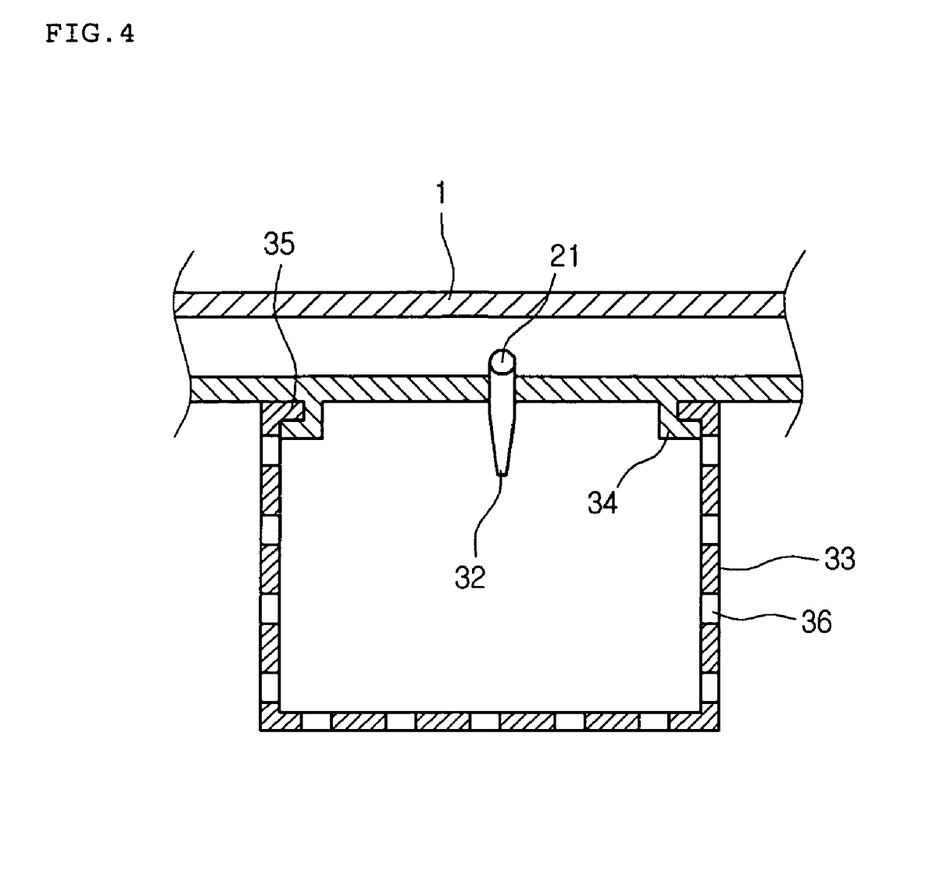
FIG. 4 is an enlarged view of a sterilizing box in FIG. 3.

FIG. 4 is an enlarged view of the sterilizing box and related components of the dishwasher according to the present invention.

Referring to FIG. 4, a catch 35 is provided at the top of the sterilizing box 33, and an insert rail 34 is formed on the top inner surface of the tub 18 opposite the catch 35. This structure allows the sterilizing box 33 to be installed when a user pushes it to the rear of the tub 18, and removed when it is pulled forward. Of course, the sterilizing box 33 may be removed for most applications in order to not interfere with the spraying force of the wash liquid. When the sterilizing box 33 is used, the hot steam discharged from the steam discharger 32 contacts the surfaces of the dishes stored in the box to completely sterilize the dishes.

This sterilizing function has the same effect as sterilizing baby bottles in boiling water, for instance, so that it can obviate the widely practiced, but tedious process of sterilizing baby bottles in boiling water.

The operation of the above-described dishwasher according to the present invention will be briefly addressed. In order to wash dishes, the door 2 is first opened and dishes are placed in the respective upper and lower dish racks 11 and 12. The dish racks 11 and 12 are restored to their original positions, after which the door 2 is closed. Of course, before the door 2 is closed, a predetermined amount of detergent may be added to the detergent cup 10.

Then, the controls 7 are manipulated by a user to input a desired dishwashing setting and begin operation of the dishwasher. The display 8 shows the operating status of the dishwasher, and the operation is begun.

When describing the operation of the dishwasher in terms of the flow sequence of wash water within the tub 18, wash liquid is first discharged from the upper and lower spray arms 14 and 15 to wash dishes in the upper and lower dish racks 11 and 12, after which the wash liquid descends to the sump 16 below. A pump (not shown) is installed in the sump 16, to pressurize and re-supply the wash liquid to the spray arms 14 and 15. While the wash liquid circulates to the spray arms 14 and 15 from the sump 16, food residue is filtered by the filter 17 to prevent excessive contamination of the wash liquid and clogging of nozzles.

At a certain point during the above operation of the dishwasher, the steam generated by the steam generator 20 passes through the steam supply pipe 21 to be supplied into the tub 18. Thus, the hot and moist characteristics of the steam ameliorate the operational reliability and efficiency of the dishwasher.

When the steam discharger 32 is provided on the top surface of the tub 18, even when wash liquid is sprayed, the wash liquid will not enter the steam discharger 32 into the steam supply pipe 21, so that operating reliability of the dishwasher is not compromised. (This is due to the possibility of food residue entering and compromising the steam supply pipe 21, should wash liquid enter the steam discharger 32.)

Also, because the steam supply pipe 21 extends vertically along the rear wall of the tub 18, it does not compromise the sealing of the tub 18.

The above description was of the dishwasher operating without the sterilizing box 33 installed inside the tub 18. When the sterilizing box 33 is installed inside the tub 18, the steam discharged from the steam discharger 32 is blown by the ventilating fan 9 to be concentrated and supplied to the inside of the sterilizing box 33, so that feeding bottles and other articles placed inside the sterilizing box 33 are completely sterilized.

The operation related to the sterilizing box 33 may be performed in a course.

Figure 5:
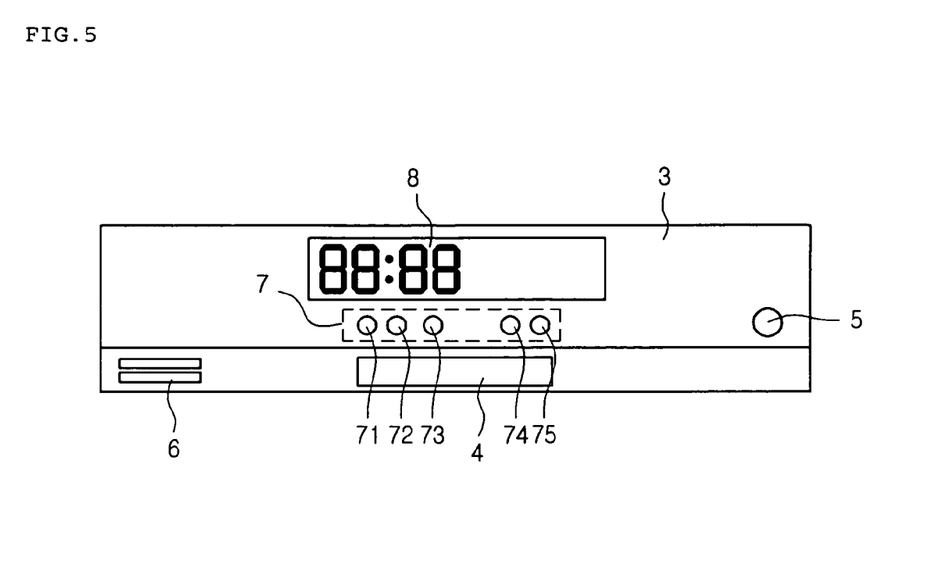
FIG. 5 is a plan view of a control panel of a dishwasher according to the present invention.

FIG. 5 is a plan view of a control panel of a dishwasher according to the present invention.

Referring to FIG. 5, as already described, the control panel 3 according to the present invention has a power switch 5, a door handle 4, controls 7, a display 8, and a steam discharge hole 6.

In detail, the controls 7 include a steam sterilizing button 71 for supplying steam into the tub 18, a normal course button 74 and a special course button 75 for implementing the respective dishwashing courses, a preset button 72 for pre-setting an operation of the dishwasher, and a pause button 73 for pausing the operation of the dishwasher in order to put more dishes in, in an emergency, or for any other reason.

The steam sterilizing button 71 is a button for supplying steam inside the sterilizing box 33, and when turned on, the steam generator 20 operates to supply steam to the inside of the sterilizing box 33. Here, the dishes stored inside the sterilizing box 33 may be not only dishes that have already been washed in the main tub 18 of the dishwasher, but may also be articles that require sterilizing, including articles handwashed by a user, wash cloths, cutting boards, and milk bottles.

Effectively, the user may place any items that require sterilizing inside the sterilizing box 33, so that the items are sterilized by the steam supplied to the sterilizing box 33. The steam sterilizing button 71 is a button that runs a steam sterilizing course which does not wash dishes, but sterilizes dishes by supplying steam inside the sterilizing box 33.

Figure 6:
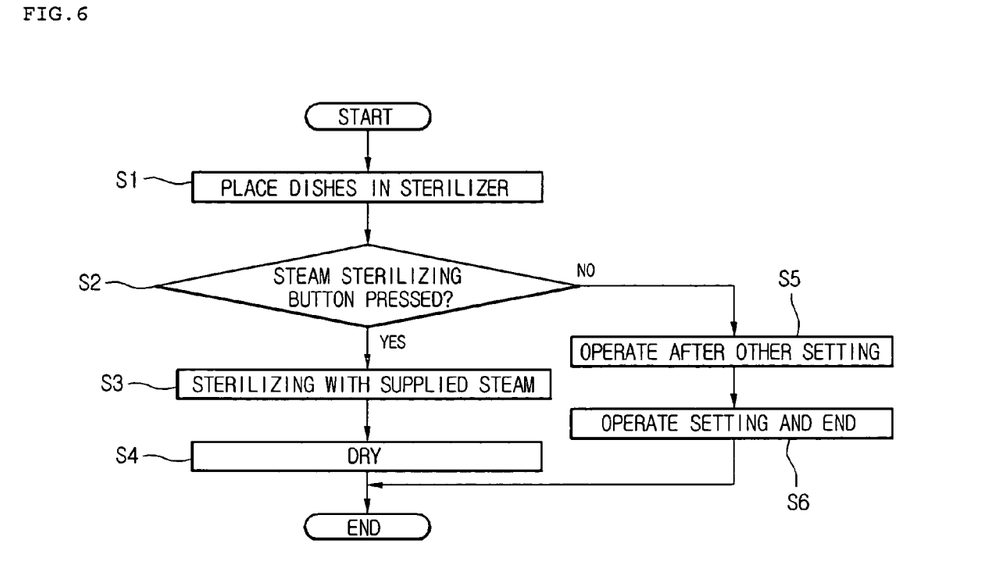
FIG. 6 is a flowchart of a steam sterilizing course according to the present invention.
Figure 7:
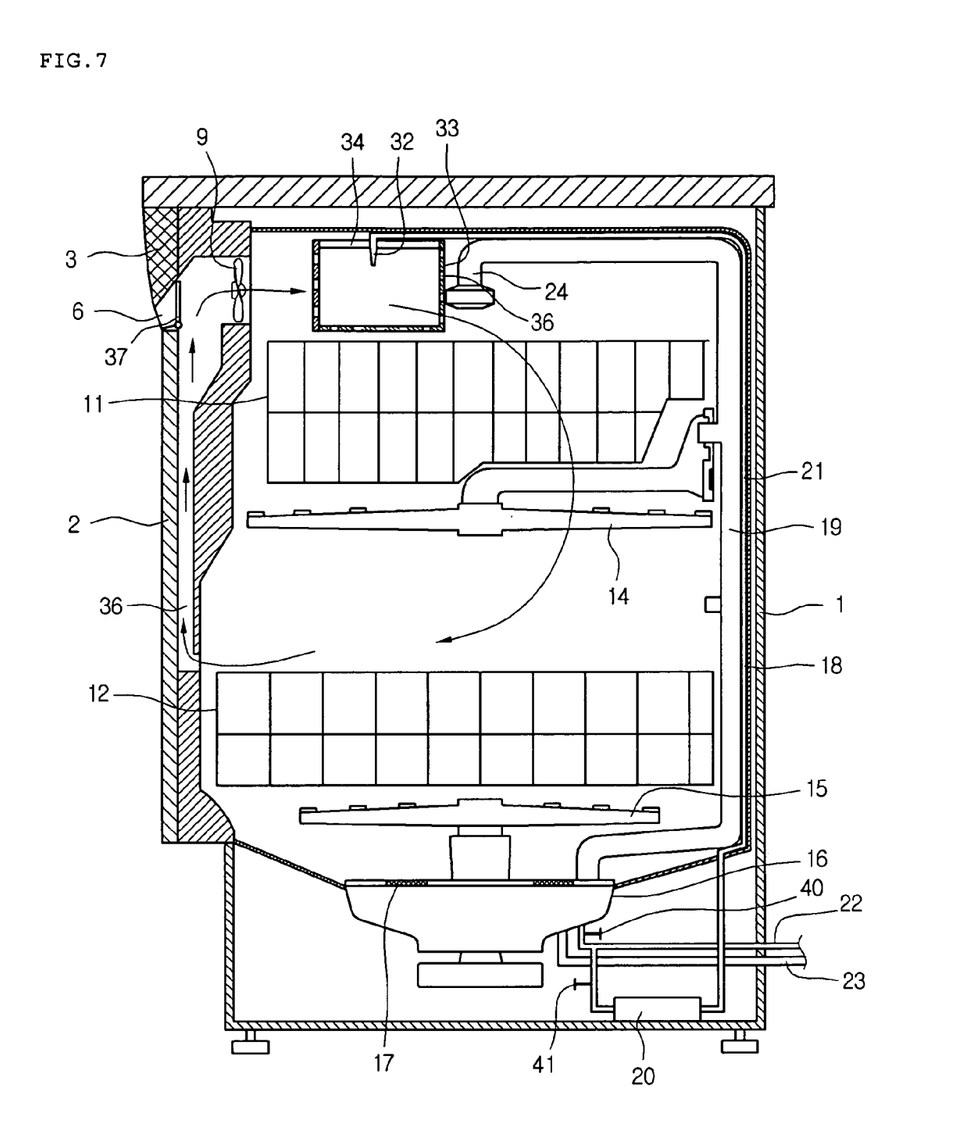
FIG. 7 is a sectional view of a dishwasher according to the present invention showing the circulation of steam within the tub.
Figure 8:
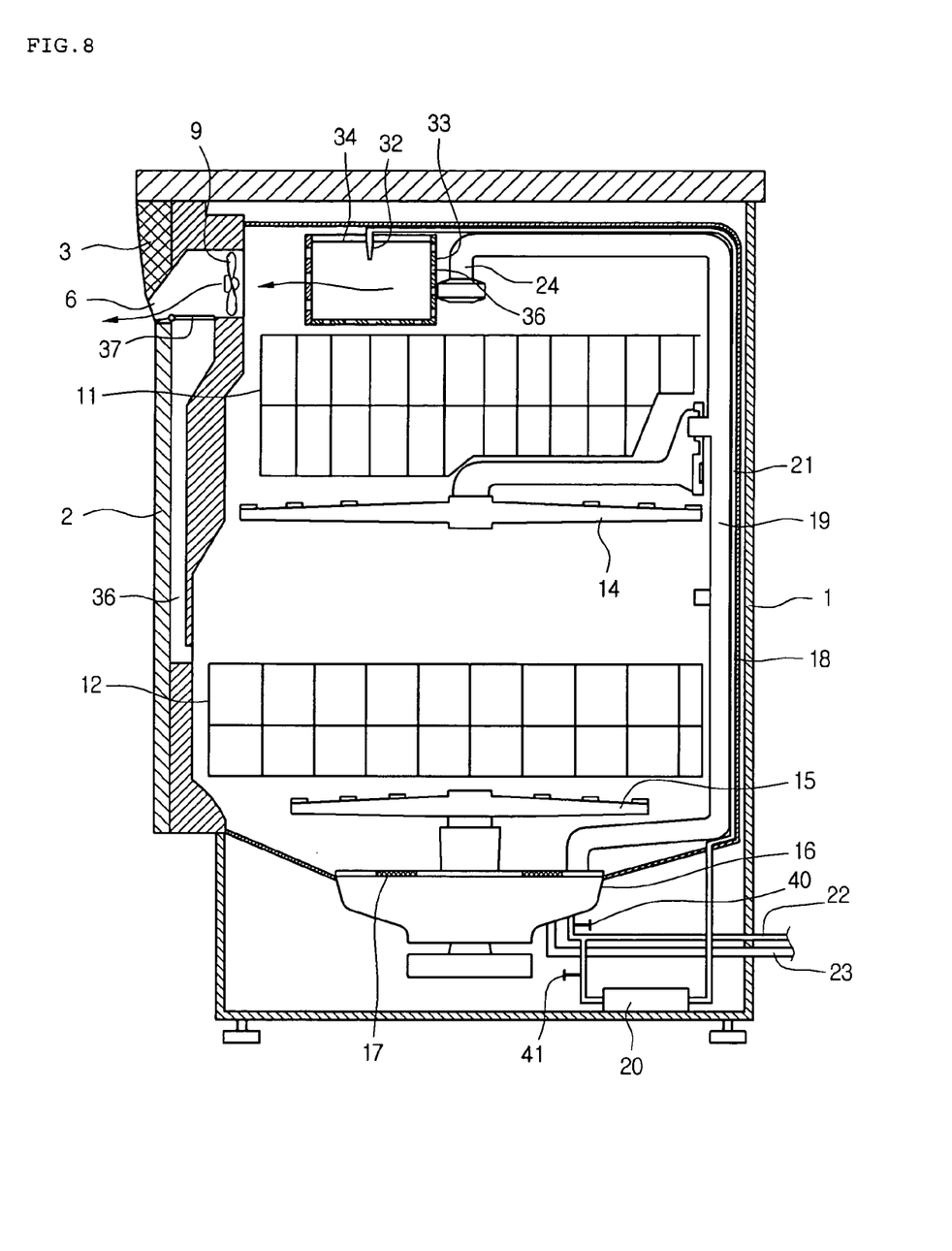
FIG. 8 is a sectional view of a dishwasher according to the present invention showing the exhausting of steam from the inside the tub to the outside.

FIG. 6 is a flowchart of a steam sterilizing course according to the present invention, FIG. 7 is a sectional view of a dishwasher according to the present invention showing the circulation of steam within the tub, and FIG. 8 is a sectional view of a dishwasher according to the present invention showing the exhausting of steam from the inside the tub to the outside.

Referring to FIGS. 6 through 8, after placing dishes in the dishwasher in step S1, a user presses the steam sterilizing button 71 in step S2 to run the sterilizing course. The items stored in step S1 are, as explained above, not only dishes that have been washed inside the dishwasher, but also hand-washed articles, wash cloths, cutting boards, etc. that require sterilizing.

If the user does not press the steam sterilizing button 71, the dishwasher operates in another mode in step S6 until completion, after the other mode is inputted in step S5.

If the user presses the steam sterilizing button 71, the steam generator 20 operates to generate steam within and supply the steam to the sterilizing box 33 through the steam supply pipe 21. The hot steam supplied into the sterilizing box 33 contacts the dishes to completely sterilize them, killing germs on their surfaces in step S3.

As shown in FIG. 7, during the supplying of steam, the damper 37 is disposed in a position that closes the steam discharge hole 6. When the steam discharge hole 6 is closed by the damper 37, the ventilating fan 9 rotates in one direction to suction air from the door passage 36 and exhaust that air into the tub. In this way, the ventilating fan 9 allows the steam discharged from the steam discharger 32 to spread throughout the inside of the tub 18.

The steam supplied in step S3, may be different according to the quantity and type of articles stored. The user can control the supply of steam. For example, the setting for the supply of steam can be set for an extended duration, in order to sterilize articles such as wash cloths and cutting boards that need prolonged exposure to steam in order to be sterilized.

If the temperature inside the tub 18 becomes hot when it becomes filled with hot steam, the steam may be exhausted to the outside.

Specifically, as shown in FIG. 8, the damper 37 moves to a position that blocks the door passage 36, and the ventilating fan 9 is rotated in a reverse direction with the damper 37 blocking the door passage 36. Thus, the ventilating fan 9 now suctions the hot air inside the tub 18 and exhausts it to the outside of the dishwasher through the steam discharge hole 6.

The steam is exhausted to prevent burns that may result from a user suddenly opening the door when the tub 18 is filled with steam supplied into the tub 18 from the steam generator 20, where the steam is usually over 100° C. Furthermore, by forcibly exhausting steam from the tub through the steam discharge hole 6, the temperature inside the tub can be lowered quickly to rapidly allow a user who is short of time to quickly remove dishes from the tub 18.

After steam is supplied into the sterilizing box 33 for sterilizing over a predetermined duration, a drying of the sterilizing box 33 is implemented by supplying cool or hot air to the sterilizing box 33 in step S4.

As described, when dishes are placed inside the dishwasher according to the present invention and the steam sterilizing button 71 is pressed, the controlling method of the dishwasher allows steam to be automatically supplied into the sterilizing box 33 to more precisely sterilize dishes inside the sterilizing box 33 within the tub 18. This steam sterilizing further sterilizes items that have already been hand-washed by a user.

Therefore, sanitation of articles in the kitchen can be improved, and the functionality of the dishwasher is improved as well.

Figure 9:
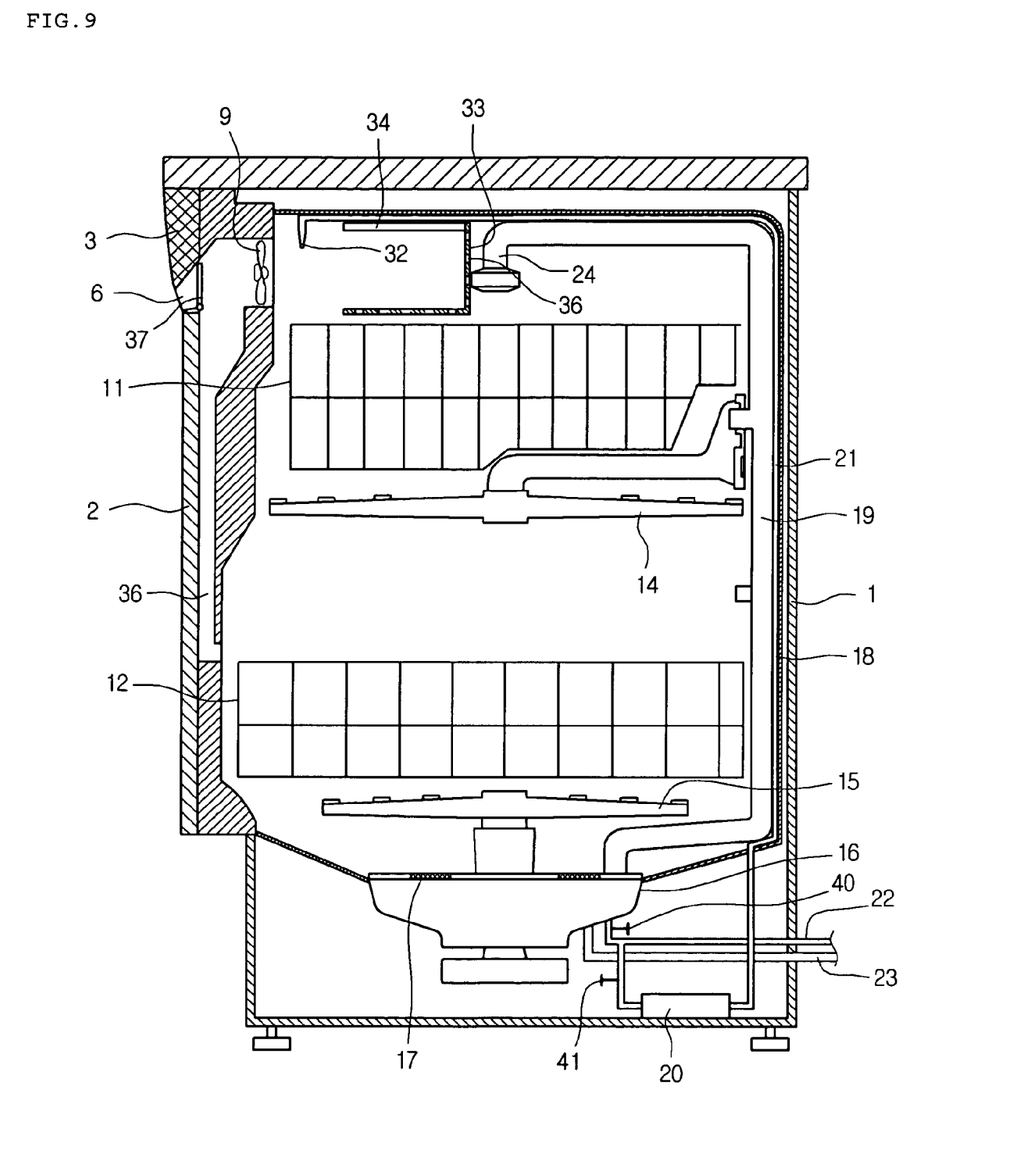
FIG. 9 is a sectional view of a dishwasher according to the second embodiment of the present invention.

FIG. 9 is a sectional view of a dishwasher according to the second embodiment of the present invention.

Referring to FIG. 9, the second embodiment of the present invention opens the front portion of the sterilizing box 33. Thus, the steam blown by the ventilating fan 9 can more easily enter the sterilizing box 33.

Also, the steam discharger 32 is positioned outside, or more specifically, in front of the sterilizing box 33. The steam discharger 32 is positioned closer to the ventilating fan 9.

Because the steam discharger 32 is positioned close to the ventilating fan 9, the steam discharged from the steam discharger 32 can be more quickly distributed inside the sterilizing box 33 and the tub 18.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A dishwasher comprising:
    a tub for holding dishes and opened at one end thereof;
    a door for selectively sealing the opened end of the tub;
    a steam generator for generating steam;
    a steam discharger for discharging the steam generated by the steam generator into the tub;
    a ventilating fan provided in the door for circulating or exhausting air inside the tub;
    a passage provided in the door for circulating the air through a rotation of the ventilating fan;
    a discharging hole formed at the door for exhausting the air to an outside of the dishwasher through a reverse rotation of the ventilating fan; and
    a sterilizing box provided in the tub for storing dishes to be sterilized by the steam discharged from the steam discharger.

2. The dishwasher according to claim 1, wherein the steam discharger is at a top of the tub.

3. The dishwasher according to claim 1, wherein the door further includes a damper for selectively opening and closing the discharging hole.

4. The dishwasher according to claim 3, wherein the damper closes the discharging hole and opens the passage when the ventilating fan circulates the air.

5. The dishwasher according to claim 3, wherein the damper opens the discharging hole and closes the passage when the ventilating fan circulates the air.

6. The dishwasher according to claim 1, wherein the steam discharger is disposed inside the sterilizing box.

7. The dishwasher according to claim 6, wherein the sterilizing box includes a plurality of through-holes formed therein.

8. The dishwasher according to claim 1, wherein the steam discharger is disposed at a front of the sterilizing box.

9. The dishwasher according to claim 1, wherein the sterilizing box includes an open front portion.

10. The dishwasher according to claim 1, wherein the sterilizing box is slidingly coupled to the tub.

11. The dishwasher according to claim 1, further comprising a dish rack for placing the dishes in, wherein the steam is provided to the dish rack after passing through the sterilizing box.

* * * * *